(12) United States Patent
Reising et al.

(10) Patent No.: US 6,893,388 B2
(45) Date of Patent: May 17, 2005

(54) METHOD OF DYNAMICALLY PRE-FASTENING A DISPOSABLE ABSORBENT ARTICLE HAVING A SLOT-AND-TAB FASTENING SYSTEM

(75) Inventors: George S. Reising, Batavia, OH (US); Michael D. Trennepohl, Cincinnati, OH (US); Darrell Ian Brown, Mason, OH (US); John Carroll Molander, Cincinnati, OH (US); Jason Matthew Prosek, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 46 days.

(21) Appl. No.: 10/632,278

(22) Filed: Aug. 1, 2003

(65) Prior Publication Data

US 2004/0023771 A1 Feb. 5, 2004

Related U.S. Application Data

(63) Continuation of application No. 10/036,633, filed on Dec. 21, 2001, now Pat. No. 6,669,618.

(51) Int. Cl.[7] ................................................ B31B 1/26
(52) U.S. Cl. ........................ 493/231; 493/394; 493/356; 493/418
(58) Field of Search .............................. 493/231, 394, 493/405, 356, 418

(56) References Cited

U.S. PATENT DOCUMENTS 6,290,687 B1 * 9/2001 Skog et al. ................. 604/391
6,432,098 B1 * 8/2002 Kline et al. ................. 604/387

FOREIGN PATENT DOCUMENTS

| WO | WO 01/87218 A2 | 11/2001 |
| WO | WO 01/87561 A2 | 11/2001 |
| WO | WO 01/87562 A2 | 11/2001 |

* cited by examiner

*Primary Examiner*—Sameh H. Tawfik
(74) *Attorney, Agent, or Firm*—Jack L. Oney, Jr.; Jay A. Krebs; Ken K. Patel

(57) ABSTRACT

A method and an apparatus for pre-fastening disposable absorbent articles having a slot-and-tab fastening system during manufacturing of the pre-fastened disposable articles, such as diapers, pull-on diapers, training pants, adults incontinence pads and the like.

2 Claims, 12 Drawing Sheets

METHOD OF DYNAMICALLY PRE-FASTENING A DISPOSABLE ABSORBENT ARTICLE HAVING A SLOT-AND-TAB FASTENING SYSTEM

CROSS REFERENCE TO RELATED APPLICATIONS

This application is a continuation of the parent application U.S. Ser. No. 10/036,633 filed on Dec. 21, 2001; U.S. Pat. No. 6,669,618.

FIELD OF THE INVENTION

The present invention relates to a high-speed-manufacturing method of pre-fastening a disposable absorbent article having a slot-and-tab fastening system.

BACKGROUND

Disposable absorbent articles such as diapers, pull-on diapers, training pants, adults incontinence pads and the like, can include a fastening system for joining the front of the article to the rear of the article. The fastening system can comprise a tab member and a slot member disclosed in U.S. patent application Ser. No. 09/143,184 filed on Aug. 28, 1998, which is incorporated by reference herein. The disclosed fastening system is a refastenable fastening system that enables the wearer or the caretaker to refasten the article during the wear to provide a more comfortable fit. The engagement of the tab and slot members can be done by the wearer or caretaker when securing the article around the wearer, or, alternatively, during manufacturing of the article to effect a pre-fasten article that is ready to be pulled on the wearer. Such manufacturing requires folding a normally flat-out article into a folded configuration and inserting the tab member into a slot of the slot member to form the pre-fastened article. However, the manufacturing of disposable absorbent article is normally a high-speed production wherein individual articles often move along a production path at a speed of hundreds feet per minute, and inserting the tab member into the corresponding slot of the slot member at such high production speeds represents a problem.

Therefore, it would be beneficial to provide a high-speed-manufacturing method of pre-fastening a disposable absorbent article having a slot-and-tab fastening system to produce a pre-fastened absorbent article having engaged tab and slot members.

SUMMARY OF THE INVENTION

In response to the difficulties and problems discussed above, a new high-speed method of pre-fastening disposable absorbent articles during manufacturing of pre-fastened disposable absorbent articles having a slot-and-tab fastening system has been discovered.

The present invention concerns a method of dynamically pre-fastening disposable absorbent articles having a slot-and-tab fastening system as the articles are driven forward at a relatively high velocity along a predetermined path. The method includes the step of providing a disposable absorbent article being folded longitudinally into a bi-fold configuration. The method further includes the step of inserting at least a portion of a tab member of the slot-and-tab fastening system through a slot of the slot-and-tab fastening system. And the method further includes the step of while holding the portion of the tab member being inserted through the slot, moving the slot member of the article opposite to the direction of insertion of the portion of the tab member until the slot of the slot member passes beyond a lip portion of the tab member to effect a complete insertion of the tab member though the slot member and to effect a closed configuration of the slot-and-tab fastening system forming a pre-fastened disposable absorbent article.

BRIEF DESCRIPTION OF THE DRAWINGS

While the specification concludes with claims particularly pointing out and distinctly claiming the subject matter, which is regarded as the present invention, it is believed that the invention will be more fully understood from the following description taken in conjunction with the accompanying drawings, in which:

DETAILED DESCRIPTION OF THE INVENTION

As used herein, the term "absorbent article" refers to devices, which absorb and contain body exudates and, more specifically, refers to devices that are placed against or in proximity to the body of the wearer to absorb and contain the various exudates discharged from the body.

The term "disposable" is used herein to describe absorbent articles, which generally are not intended to be laundered or otherwise restored or reused as absorbent articles (i.e., they are intended to be discarded after a single use and, preferably, to be recycled, composted or otherwise discarded in an environmentally compatible manner).

The term "diaper" refers to an absorbent article generally worn by infants and incontinent persons about the lower torso and typically having a fastening system to connect a back waist region with the front waist region in a closed configuration so as to provide lateral tensions about the circumference of the diaper to hold the diaper on the wearer.

The term "pre-fastened disposable article" or "pre-fastened article" or "pre-fastened diaper" refers herein to disposable absorbent articles, which are provided to consumer in a pre-fastened configuration of the fastening system (i.e., the fastening system is engaged to form a closure) of the article and, which are intended to be put on the wearer through the legs of the wearer.

The terms "pull-on diaper" and/or "training pants" refer herein to disposable absorbent articles typically having a fixed, closed configuration around the waist of the wearer and, which are intended to be put on the wearer by pulling the article through the legs of the wearer.

For ease of understanding, much of the following description with respect to disposable absorbent articles comprising a slot-and tab fastening system will be made in terms of a diaper 20 disclosed in U.S. patent application Ser. No. 09/143,184 filed on Aug. 28, 1998, which is incorporated by reference herein.

Figure 1:
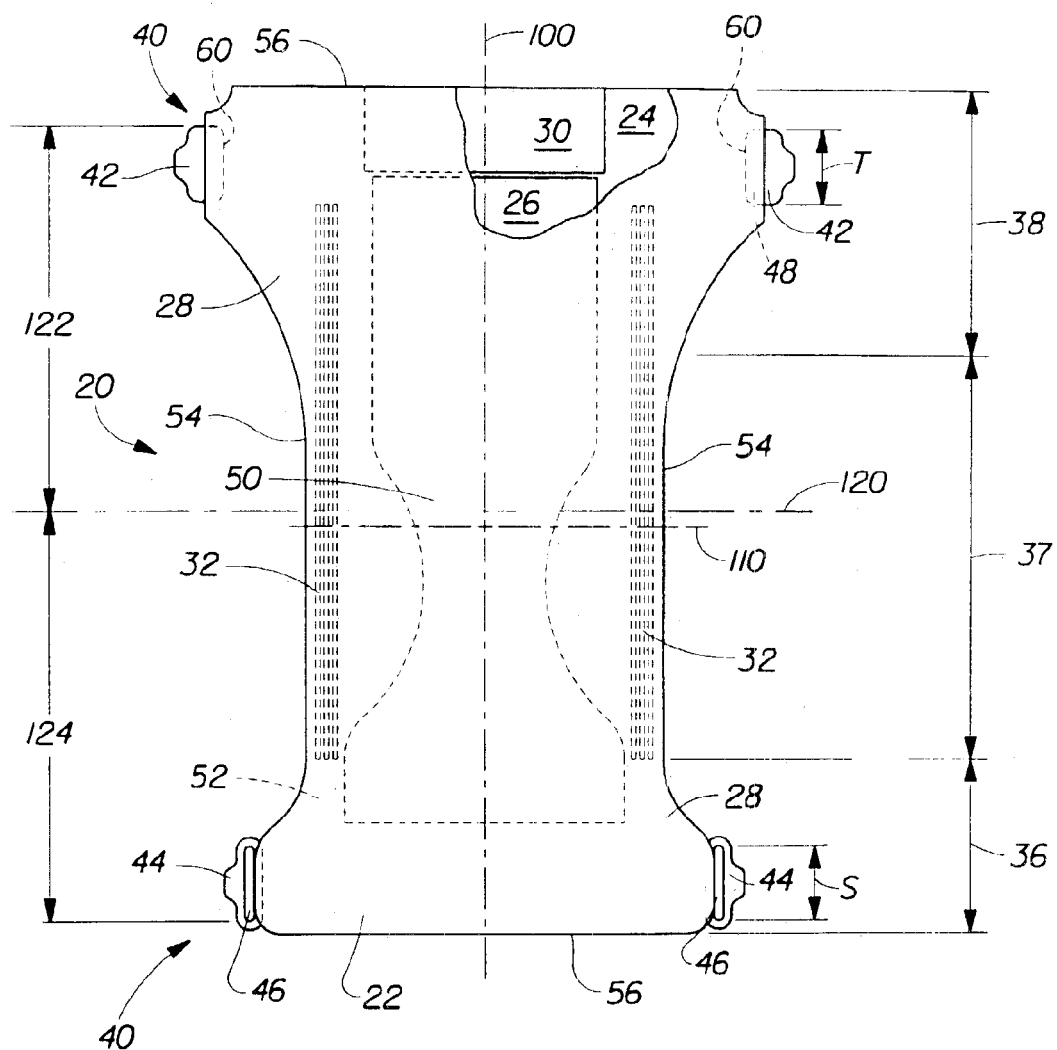
FIG. 1 is a plan view of a diaper having a fastening device comprising a tab member and a slot member in its flat out, uncontracted state with the body-facing surface oriented toward the viewer.

FIG. 1 illustrates a plan view of one embodiment of the diaper 20 in its flat-out, uncontracted state (i.e., with elastic induced contraction pulled out) including a slot-and-tab fastening system 40. The portion of the diaper 20 that faces or contacts the wearer, the inner surface 50, is oriented towards the viewer. As shown in FIG. 1, the diaper 20 preferably comprises a liquid pervious topsheet 22; a liquid impervious backsheet 24 joined with the topsheet 22; an absorbent core 26 positioned between the topsheet 22 and the backsheet 24; side panels 28; leg cuffs 32; a waist feature 30 and the slot-and-tab fastening system 40.

The diaper 20 is shown in FIG. 1 to have an outer surface 52, an inner surface 50 opposed to the outer surface 52, first waist region 36, a second waist region 38 opposed to the first waist region 36, a crotch region 37 positioned between the first waist region 36 and the second waist region 38. The diaper 20 also has longitudinal edges 54 and end edges 56. The inner surface 50 of the diaper 20 generally comprises that portion of the diaper 20 that is positioned adjacent to the wearer's body during use (i.e., the inner surface 50 generally is formed by at least a portion of the topsheet 22 and other components joined to the topsheet 22). The outer surface 52 generally comprises that portion of the diaper 20 that is positioned away from the wearer's body (i.e., the outer surface 52 generally is formed by at least a portion of the backsheet 24 and other components joined to the backsheet 24). The diaper 20 also has a longitudinal centerline 100 and a lateral centerline 110.

Figure 2:
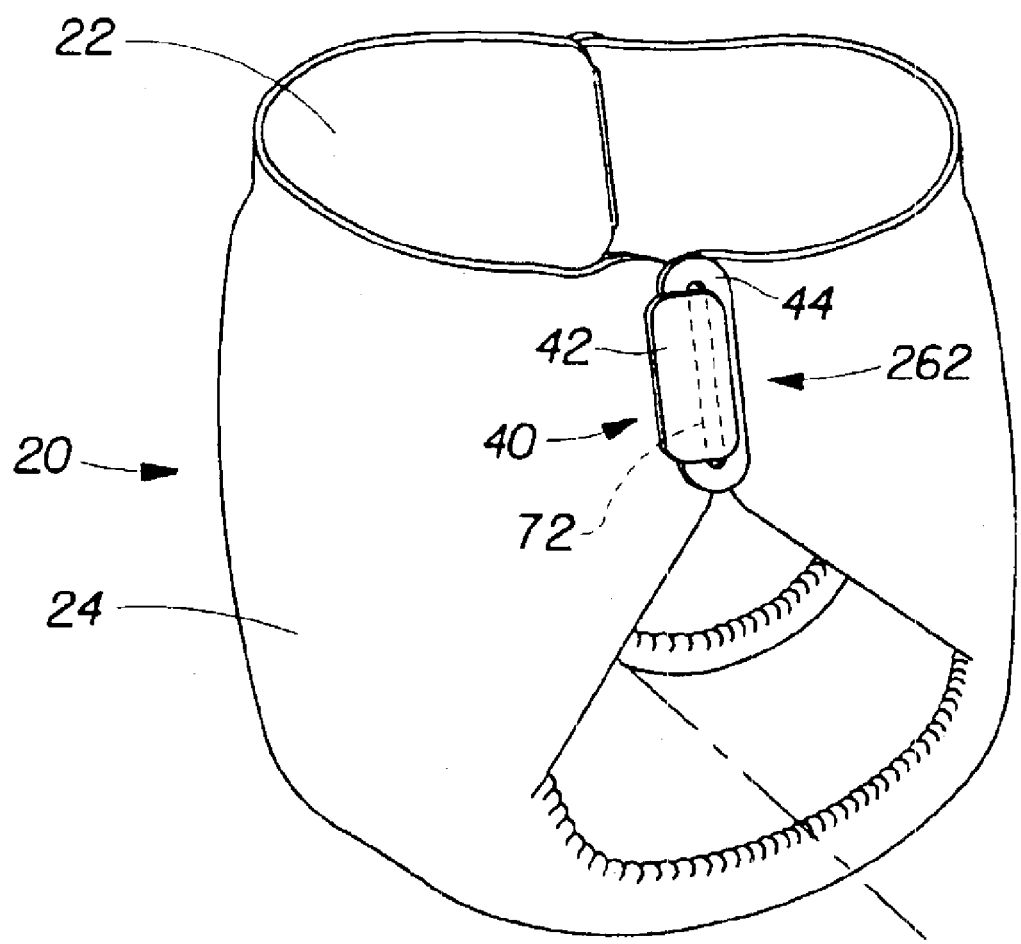
FIG. 2 is a perspective view of the diaper of FIG. 1, wherein the tab member is engaged with the slot member by passing the tab member through the slot of the slot member.

The slot-and-tab fastening system 40 joins at least a portion of the first waist region 36 of the diaper 20 with at least a portion of the second waist region 38, preferably to form leg and waist openings. As shown in FIGS. 1 and 2, the fastening system 40 can comprise a tab member 42 and a slot member 44.

Figure 3:
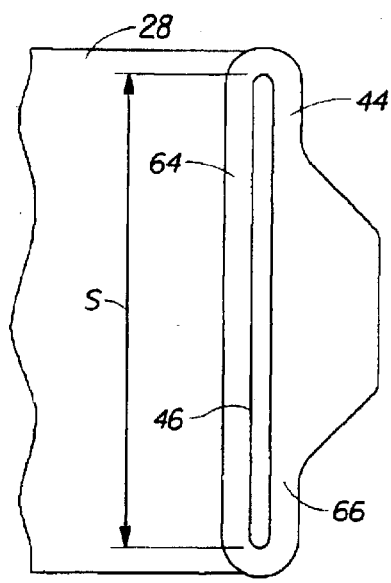
FIG. 3 is a plan view of the slot member of the diaper of FIG. 1.
Figure 4:
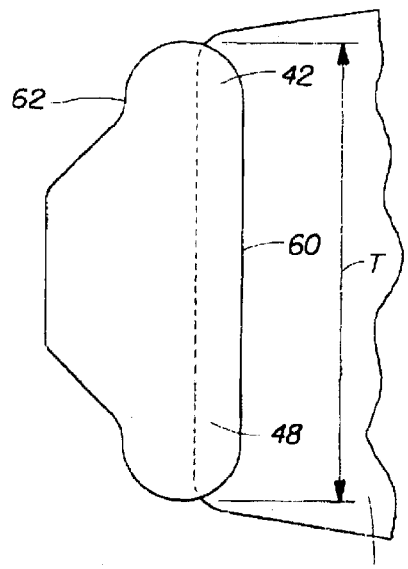
FIG. 4 is a plan view of the tab member of the diaper of FIG. 1.

The slot member 44, shown in FIG. 3, includes an inboard portion 64 attached to the side panel 28, an outboard portion 66 and a slot 46 disposed between the inboard portion 64 and the outboard portion 66. The slot 46 has a length S.

Figure 5:
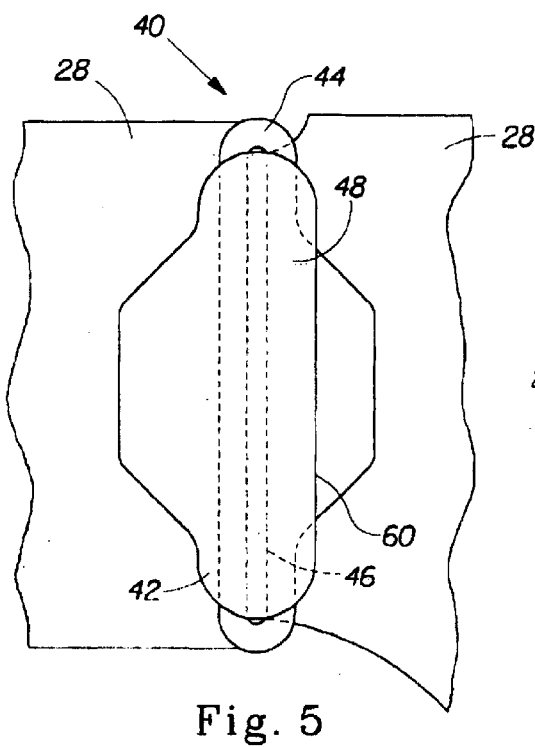
FIG. 5 is a plan view of the engaged tab and slot members.

As shown in FIG. 5, the tab member 42 preferably includes a generally elongate member having a length T, a proximal edge 60, a distal edge 62, a lip portion 48 generally adjacent at least a portion of the proximal edge 60. The length T of the tab member 42 should be sized to fit through the slot 46 of the slot member 44 with little or no bending or deformation of either component. The lip portion 48 is that portion of the tab member 42 which is not joined directly to the underlying structure of the article to which the tab member 42 is attached. The lip portion 48 should lift away from the underlying structure of the article so that it can be positioned in an overlapping configuration with at least a portion of the outboard portion 66 of the slot member 44 when in use (shown in FIGS. 5 and 6).

Figure 6:
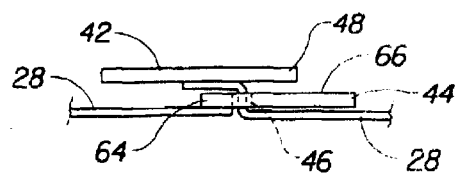
FIG. 6 is an end view of the engaged tab and slot members shown in FIG. 5.
Figure 7:
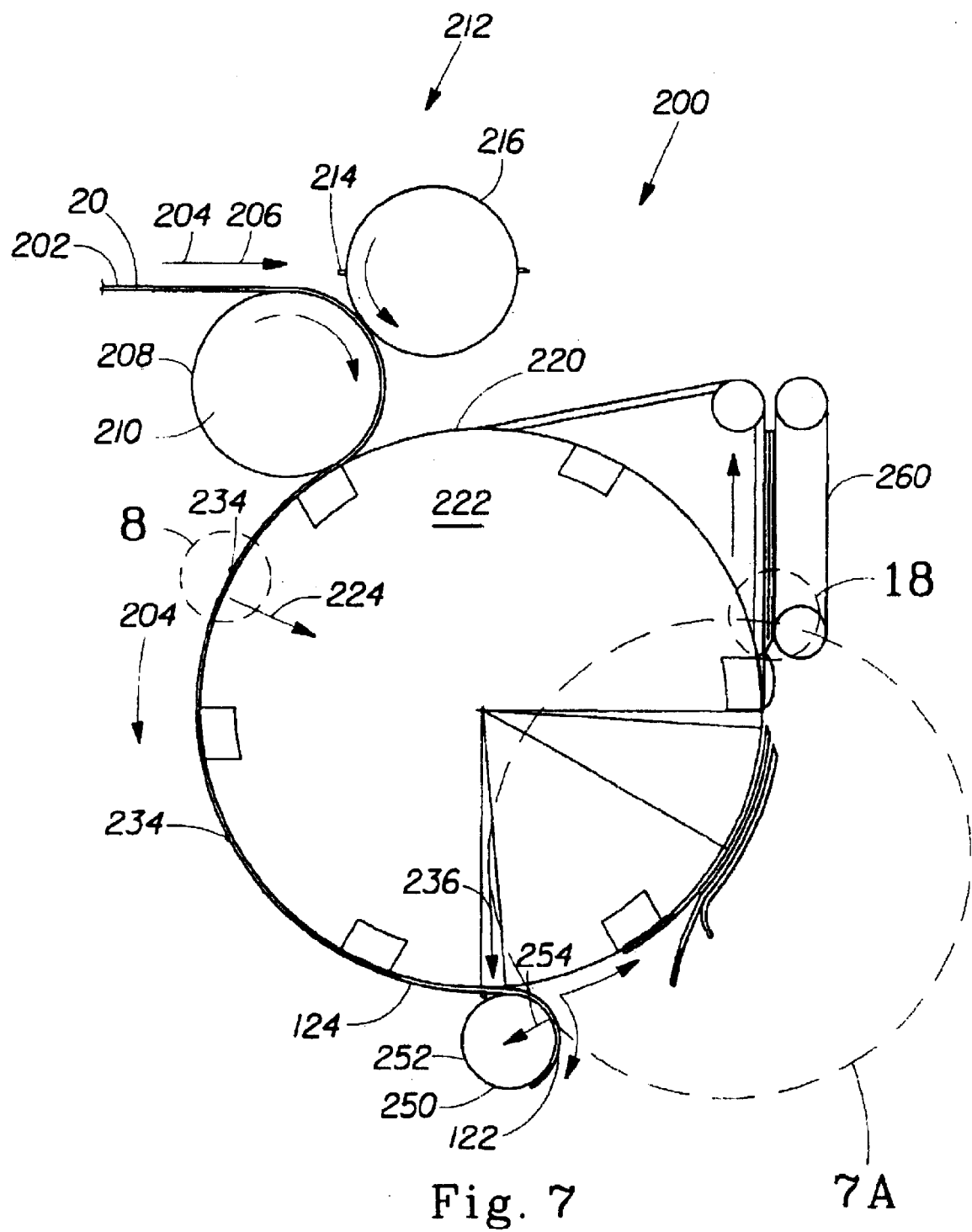
FIG. 7 is a simplified front elevation view of one embodiment of an apparatus of the present invention.
Figure 7A:
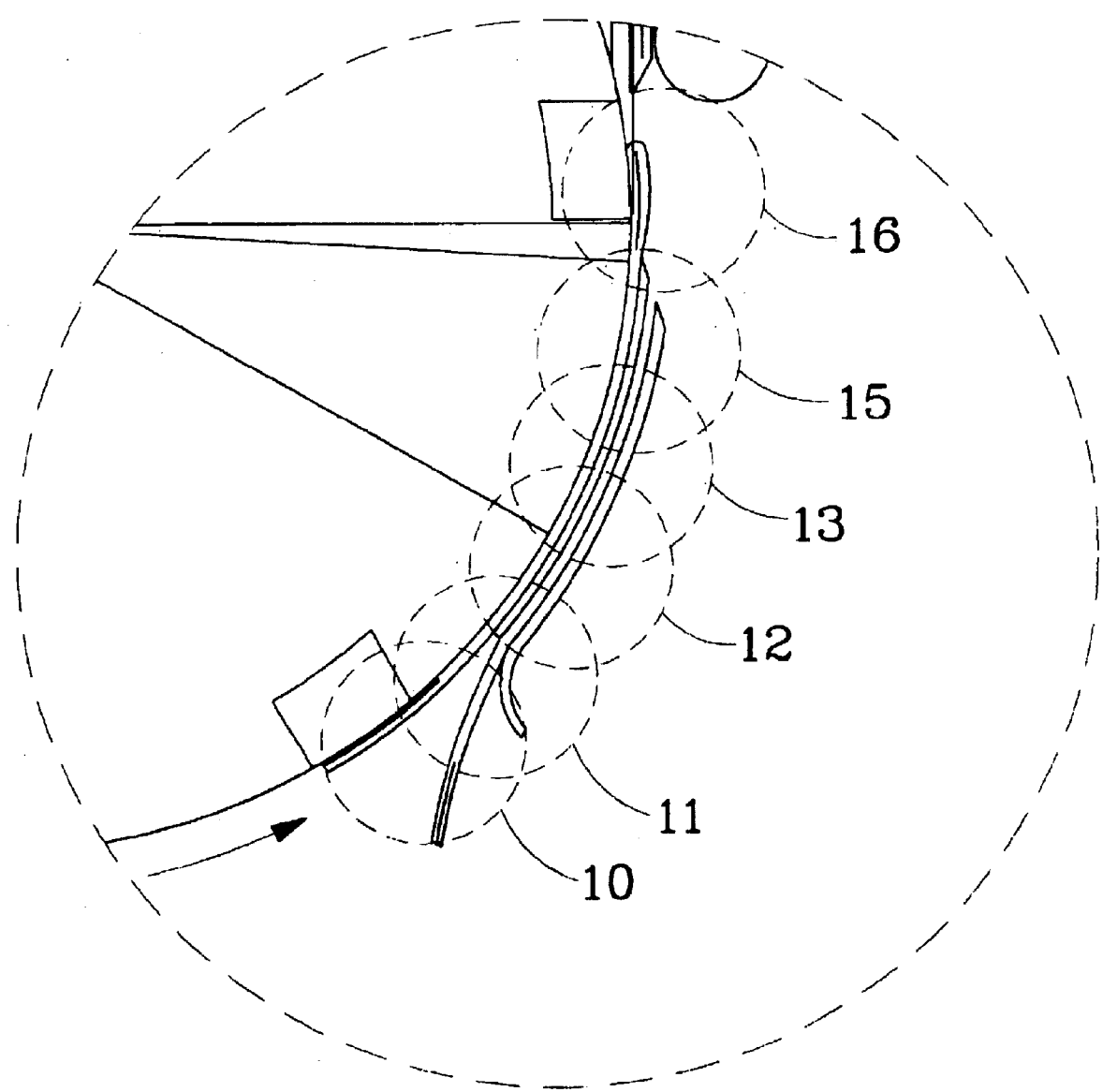
FIG. 7a is a magnified, partial, front elevational view of the circled area 7a shown in FIG. 7.

As shown in FIG. 6, the fastening system 40 can be fastened by passing the tab member 42 completely through the slot 46 of the slot member 44. Once the tab member 42 has been passed through the slot member 44, as shown in FIGS. 7, the lip portion 48 of the tab member 42 is rotated into a plane generally parallel with the plane of the slot member 44 such that at least a part of the lip portion 48 is overlapping at least a part of the outboard portion 66 of the slot member 44. In this configuration, the lip portion 48 of the tab member 42 will prevent the tab member 42 from slipping back through the slot 46 and disengaging the fastening system 40.

Referring to FIG. 1, the diaper 20 has a longitudinal centerline 100 dividing the diaper 20 laterally equally between two opposing longitudinal edges 54, and a lateral centerline 110 dividing the diaper 20 longitudinally equally between two opposing end edges 56. The diaper 20 also has fastening centerline 120 dividing the diaper 20 longitudinally equally between the tab member 44 and the slot member 42 so when the diaper 20 is folded along the fastening centerline 120, the tab member 42 and the slot 46 of the corresponding slot member 44 are generally aligned for at least partial insertion of the tab member 42 into the slot 46. The fastening centerline 120 divides the diaper 20 into a leading part 122 having the tab members 42 and a trailing part 124 trailing the leading part 122 and having the slot members 44. The fastening centerline 120 may or may not coincide with lateral centerline 110.

Figure 8:
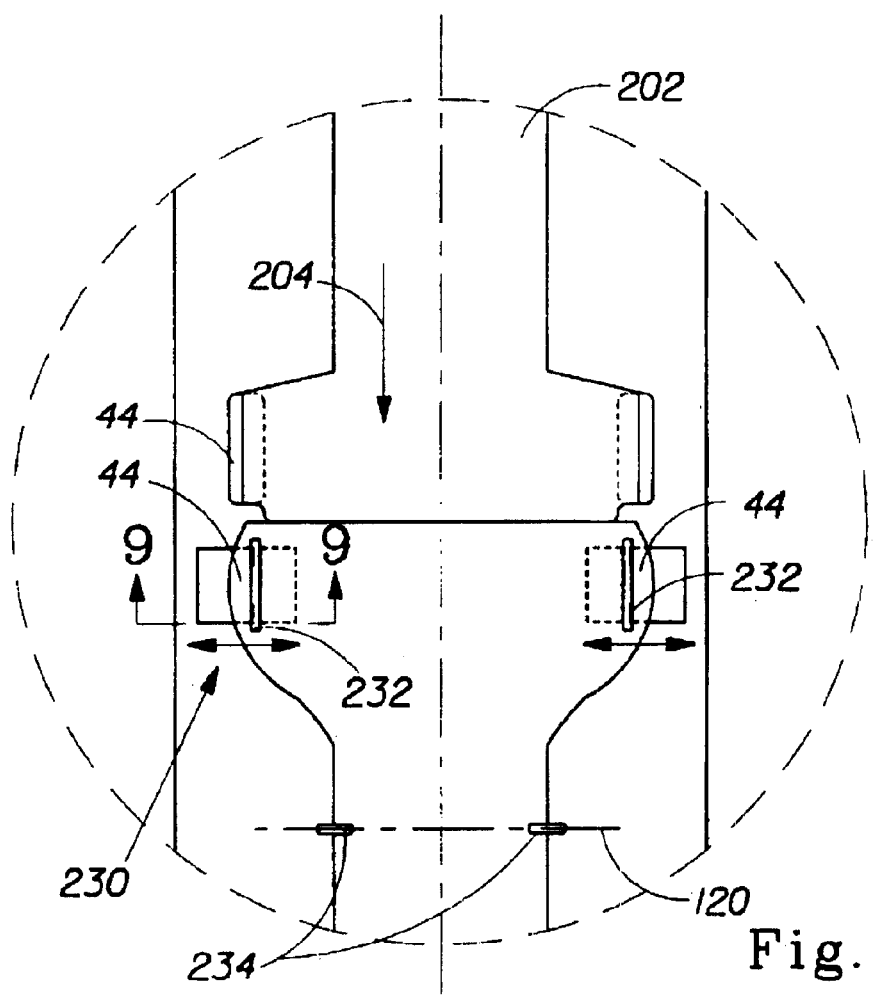
FIG. 8 is fragmental, simplified side plan view taken along arrow 8 of the apparatus of FIG. 7, showing two slot locators.

The diaper 20 can be folded along the fastening centerline 120 into two opposing parts with the topsheet 22 facing inside of the folded article 20 (FIG. 2) and with the respective tab members 44 and slot members 42 facing each other and properly aligned to form an engagement by inserting the tab member 44 through the slot 46 of the corresponding slot member 42 by a new process of the present invention. The new process can be provided by an apparatus 200, one embodiment of which is shown in FIG. 7 as a simplified, front elevation view. FIG. 8 shows a fragmental, simplified side plan view of the apparatus 200 taken along arrow 8 of FIG. 7. The new process is a dynamic process, meaning herein that the steps of the new process are performed when the apparatus 200 is in motion, preferably at a predetermined velocity, which can range from about 200 feet per minute to about 1,000 feet per minute.

Referring to FIGS. 1, 7 and 8, a web 202 preferably comprising a multiplicity of disposable absorbent articles 20, can move along a predetermined path 204 at a predetermined velocity 206. The web 202 can be generally flat under tension directed in the direction of the predetermined path 204. The articles 20 can be oriented in relation to the predetermined path 204 such that the leading part 122 of the article 20 leads the trailing part 124 of the article 20. The web 202 can be deposited onto a peripheral surface 208 of an anvil roll 210 of a rotary cutter 212 such that the inner surface 50 of the diaper 20 is facing the peripheral surface 208 of the anvil roll 210. The web 202 can be held flat against the peripheral surface 208 by an anvil roll holding force 218, which can be provided by any suitable means including mechanical clamps, belts, electrostatics, magnetism, vacuum and the like. In one embodiment of the present invention, the anvil roll holding force can be provided by vacuum communicating through openings in the peripheral surface 208 of the anvil roll 210. The web 202, held flat against the peripheral surface of the anvil roll 210, can be cut into individual articles 20 by a cutter 214 rotating with a cutter roll 216 of the rotary cutter 212.

After the cut, the individual articles 20 can continue to be held flat against the peripheral surface 208 of the anvil roll 210 by the anvil roll holding force 218 until the individual articles 20 can be transferred onto a peripheral surface 220 of a drum 222 disposed adjacent the anvil roll 210 and rotating in the direction of the predetermined path 204. During the transfer, the anvil roll holding force 218 can be turned off and a drum holding force 224 turned on to hold the individual article 20, now facing the peripheral surface 220 of the drum 222 with the outer surface 52 including the backsheet 24 of the article 20. The drum holding force 224 can be provided by the same means as the anvil roll holding force 218 described herein above. In one embodiment of the present invention, the drum holding force 224 can be provided by vacuum communicating through the openings in the peripheral surface 220 of the drum 222. Individual articles 20 can continue to be held flat by the drum 222 under tension directed in the direction of the predetermined path 204.

In addition to the drum holding force 224, the articles 20 can be held to the peripheral surface 220 of the drum 222 along a fastening centerline 120 of the article 20, dividing the diaper 20 longitudinally equally between the tab member 44 and the slot member 42, so when the diaper 20 is folded along the fastening centerline 120, the tab member 42 and the slot 46 of the corresponding slot member 44 are generally aligned for at least partial insertion of the tab member 42 into the slot 46. The article 20 can be held along the fastening centerline 120 by any suitable means including a single continuous clamp or two or more separate clamps disposed along the fastening centerline 120. In one embodiment of the present invention, the article 20 can be held by two centerfold clamps 234 (see FIG. 8) disposed along the fastening centerline 120 for attaching the article 20 along the fastening centerline 120 to the peripheral surface 220 of the drum 222. The center-fold clamps 234 can be activated by any suitable means capable of attaching and detaching the article 20 along the fastening centerline 120, including electro-mechanical, pneumatic, hydraulic, servomotors, cams and the like.

Figure 9:
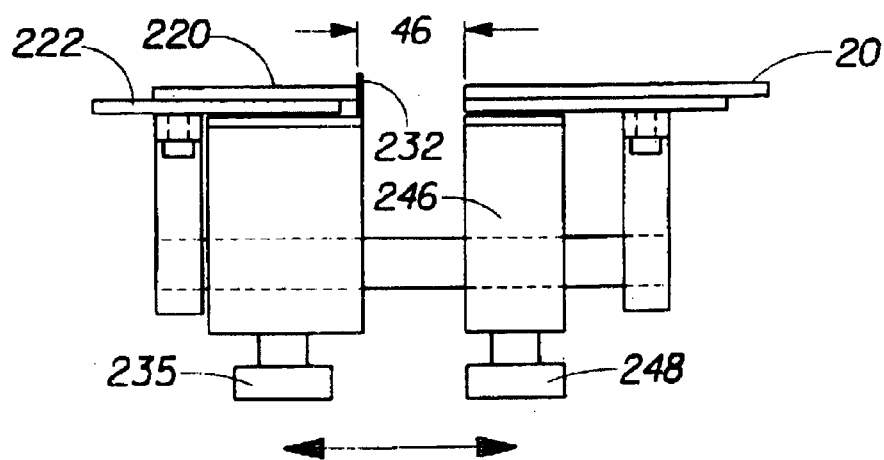
FIG. 9 is a cross-sectional view, taken along lines 9—9, of the slot locator shown in FIG. 8.

After depositing the article 20 onto the drum 222, the slots 46 of the slot members 44 of the article 20 can be located on the peripheral surface 220 of the rotating drum 222 at a target position 230 by any suitable mechanical device capable of engaging with the slots 46 and moving the slots 46 transversely to the predetermined path 204 into the target position 230. The target position 230 is a position of the slot member 44 on the peripheral surface 220 of the drum 220 suitable for engaging with the corresponding tab members 42 of the article 20. In one embodiment of the present invention shown in FIGS. 8 and 9, each slot 46 can be positioned into the target position 230 by a slot locator 232. The slot locator 232 can be actuated by any suitable means, including electro-mechanical, pneumatic, hydraulic, servomotors, and the like. In one embodiment of the present invention shown in FIG. 9, the slot locator 232 can be actuated by a cam (not shown) engaging a cam follower 235 attached to the slot locator 232.

The apparatus 200 of the present invention can further include a peel-off roll 250 disposed adjacent the drum 222, preferably at a 6 o'clock position of the drum 222, for separating the leading part 122 of the article 20 from the peripheral surface 220 of the drum 222 and transferring the leading part 122 of the article 20 onto the peripheral surface 252 of the peel-off roll 250. Prior to this, the leading part 122 can be separated from the peripheral surface 220 of the drum 222 by deactivating the drum holding force 224 under the leading part 122 of the article 20 and activating a drum separating force 236 under the leading part 122 of the article 20. The drum separating force 236 can be provided by any suitable means including mechanical, electrostatic, magnetic and the like. In one embodiment of the present invention, the drum separating force 236 can be provided by compressed air vented though the holes in the peripheral surface 220 of the drum 222.

After the leading part 122 is separated from the drum 222, the leading part 122 can be transferred onto and held against a peripheral surface 252 of the peel-off roll 250 by means of a peel-off roll holding force 254. The peel-off roll holding force 254 can be provided by the same means as the anvil roll holding force 218 described herein above. In one embodiment of the present invention, the peel-off roll holding force 254 can be provided by vacuum communicating through the openings in the peripheral surface 252 of the peel-off roll 250.

Figure 10:
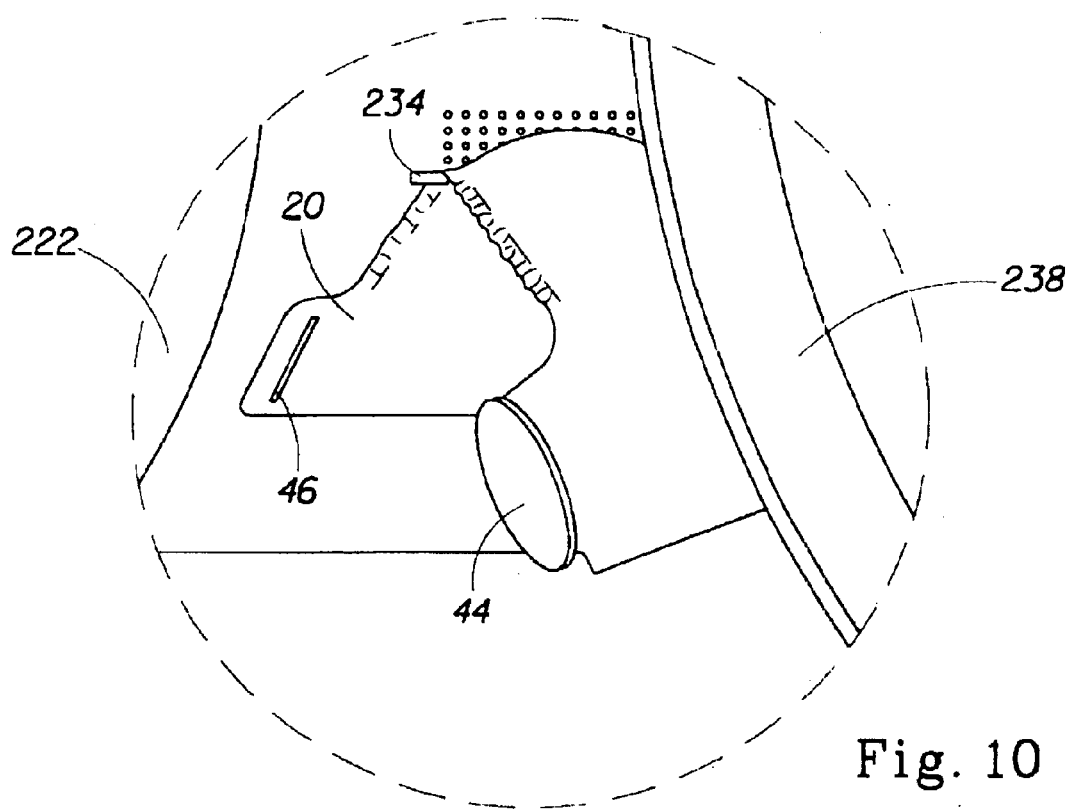
FIG. 10 is an enlarged view of circled area 10 of FIG. 7a, showing the diaper in its instant position just prior to thrusting a leading part of the diaper pad against a stationary folding board of the apparatus of the present invention.

After the leading part 122, is transferred onto the peel-off roll 250, the peel-off roll holding force 254 can be substituted by a peel-off roll separating force 256, similar to the drum separating force 236, described herein above. The peel-off roll separating force 256 can separate the leading part 122 from the peel-off roll 250, and a centrifugal force, resulting from the rotation of the drum 222, can extend the leading part 122 radially from the peripheral surface 220 of the drum 222. (See FIG. 10.)

Figure 11:
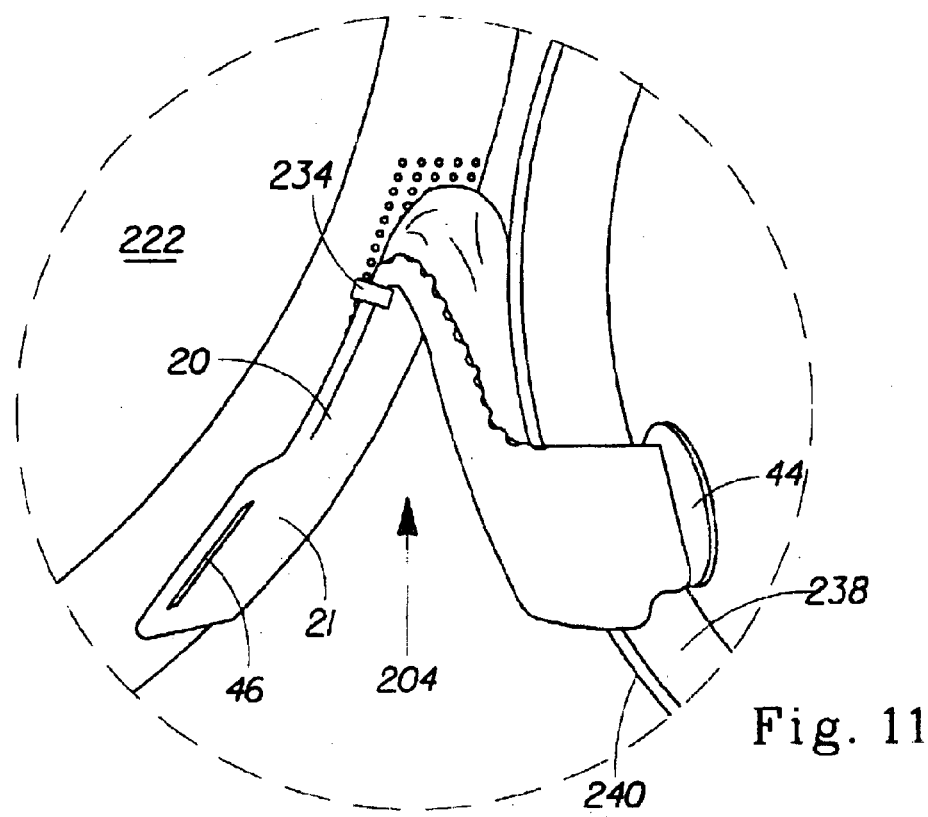
FIG. 11 is an enlarged view of circled area 11 of FIG. 7a, showing the diaper in its instant position of thrusting the leading part of the diaper pad against the stationary folding board of the apparatus of the present invention.
Figure 12:
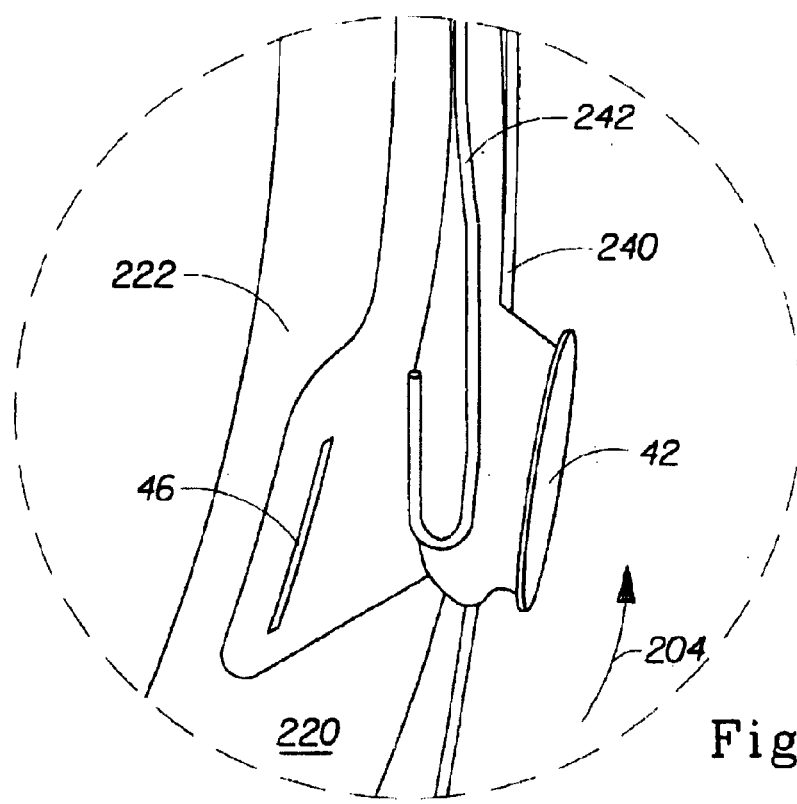
FIG. 12 is an enlarged view of circled area 12 of FIG. 7a, showing the diaper in its instant position having the tab member intercepted between a guiding rail and the folding board.

Next, referring to FIG. 11, under continuing rotation of the drum 222, the leading part 222 extending from the peripheral surface 220 of the drum 222 can move into contact with a stationary folding board 238 situated along the predetermined path 204 to form a bi-fold configuration 21 of the diaper 20, wherein the article 20 is folded longitudinally. During the move into contact of the leading part 122 with the folding board 238, each tab member 42 of the leading part 122 folds at least partially around the folding board 238, preferably around a longitudinal edge 240 of the folding board 238. Further, referring to FIG. 12, under continuing rotation of the drum 222, the tab member 42 can pass between the longitudinal edge 240 and a stationary guiding rail 242 disposed adjacent the longitudinal edge 240 and extending along the predetermined path 204.

Figure 13:
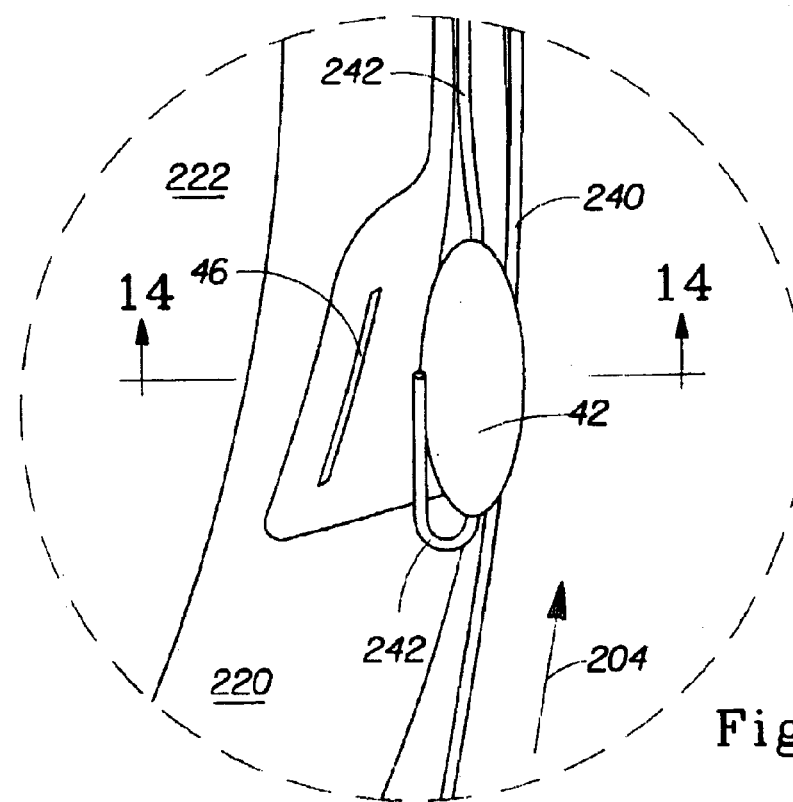
FIG. 13 is an enlarged view of circled area 13 of FIG. 7a, showing the diaper in its instant position of aligning the tab member with a slot of the slot member.
Figure 14:
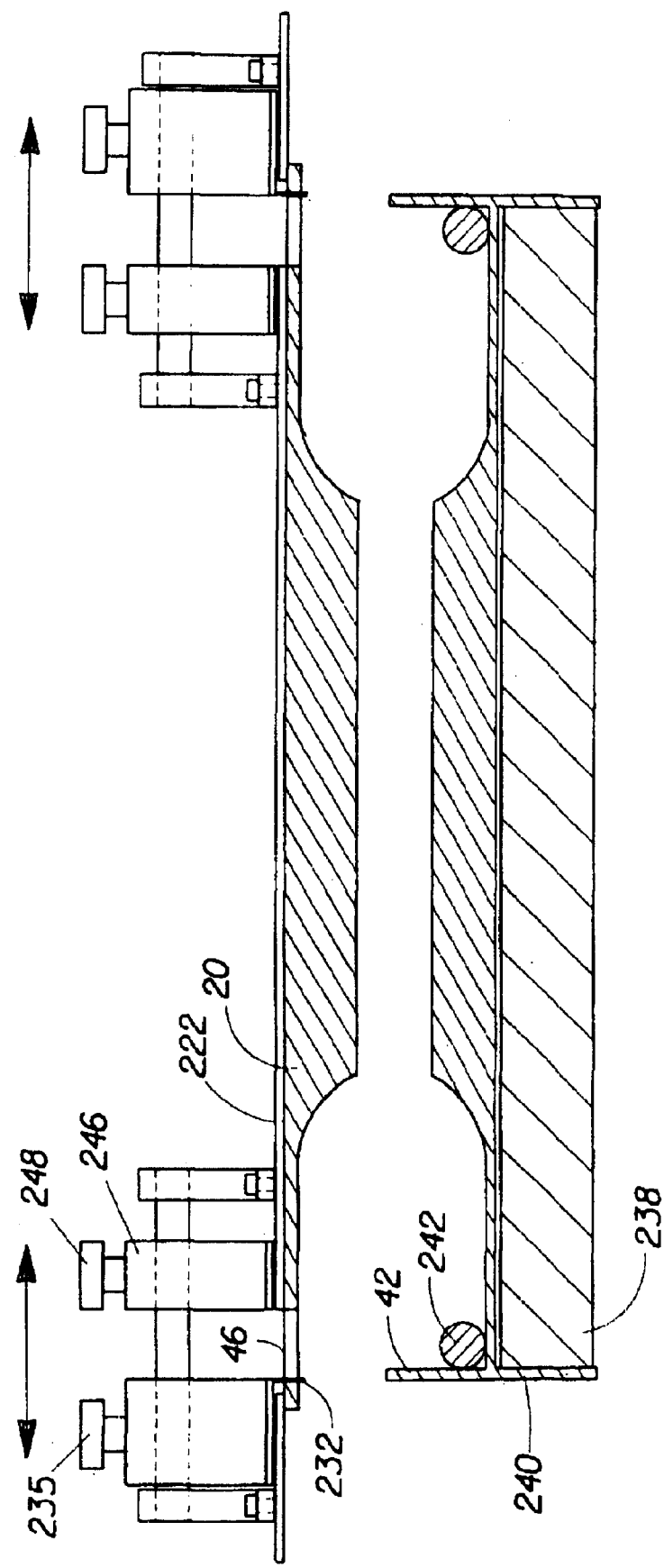
FIG. 14 is a cross-sectional view, taken along lines 14—14 in FIG. 13, showing alignment of the tab member with the slot of the slot member by the guiding rail and the folding board.

Further, under continuing rotation of the drum 222, the tab member 42 being passed between the longitudinal edge 240 of the folding board 238 and the guiding rail 242, can be guided by the longitudinal edge 240 of the folding board 238 and the guiding rail 242 to align the tab member 242 with the slot 46 as shown in FIGS. 13 and 14, where FIG. 14 is a cross-sectional view taken along lines 14—14 of FIG. 13. (As described herein above, the slot 46 has been aligned and held in the target position by the slot locator 132.)

Figure 15:
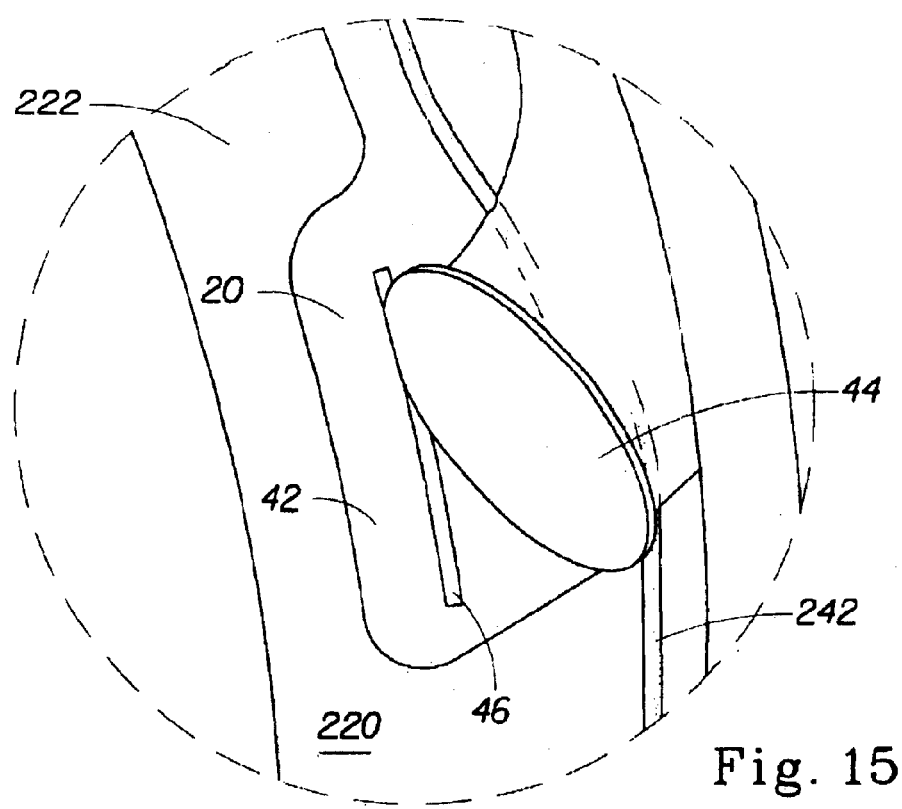
FIG. 15 is an enlarged view of circled area 15 of FIG. 7a, showing the diaper in its instant position of initially inserting the tab member into the slot of the slot member.
Figure 16:
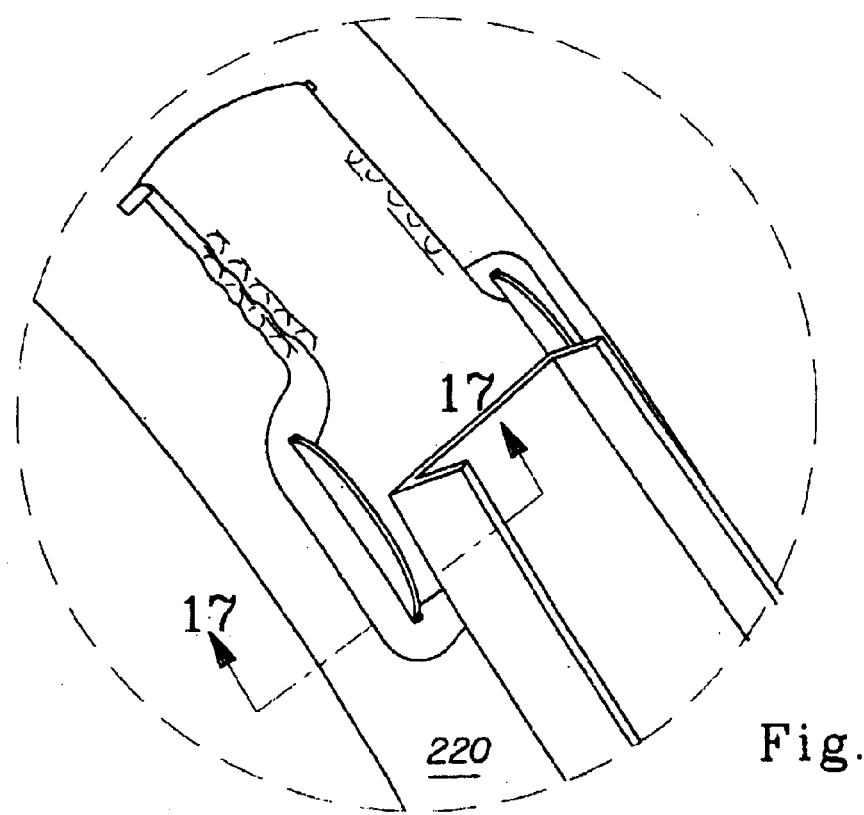
FIG. 16 is an enlarged view of circled area 16 of FIG. 7a, showing the diaper in its instant position of further inserting the tab member into the slot and attaching the inserted portion of the tab member to the drum by a tab-clamping device.
Figure 17:
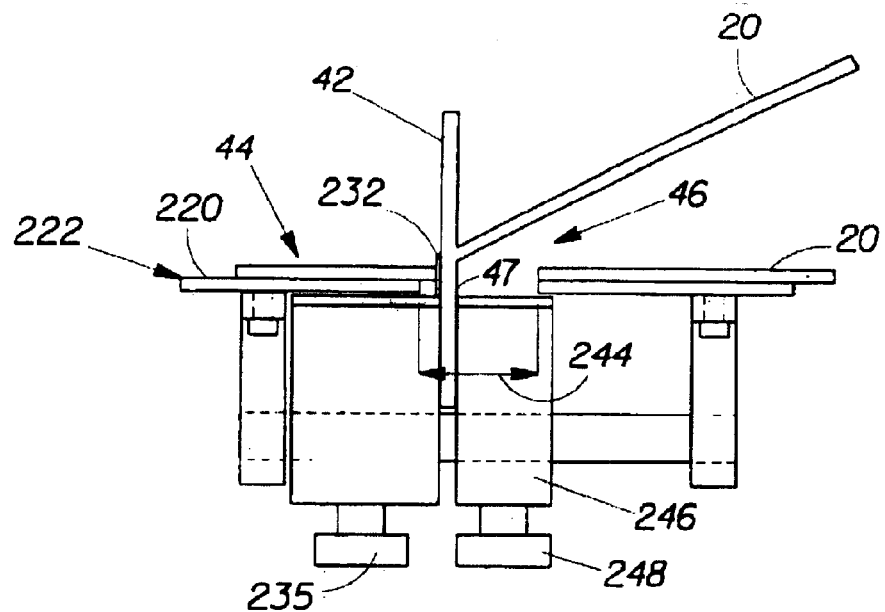
FIG. 17 is cross-sectional view, taken along lines 17—17 in FIG. 16, illustrating the tab-clamping device attaching the tab member to the drum.

Further, as shown in FIGS. 15 and 16, under continuing rotation of the drum 222, the tab member 42 can be further guided by the longitudinal edge 240 of the folding board 238 and the guiding rail 242 to insert at least a portion 47 (see FIG. 17 showing a cross-sectional view taken along lines 17—17 of FIG. 16) of the tab member 42 through the slot 46 of the article 20 into an opening 244 in the peripheral surface 220 of the drum 222. FIG. 17 also shows the next step of attaching the portion 47 of the tab member 44 to the drum 222 by a clamp 246. As the slot locator 232, described herein above, the clamp 246 can be actuated by any suitable means, including electro-mechanical, pneumatic, hydraulic, servomotors, and the like. In one embodiment shown in FIG. 17, the clamp 246 can be actuated by a cam (not shown) engaging a cam follower 248 attached to the clamp 246.

Figure 18:
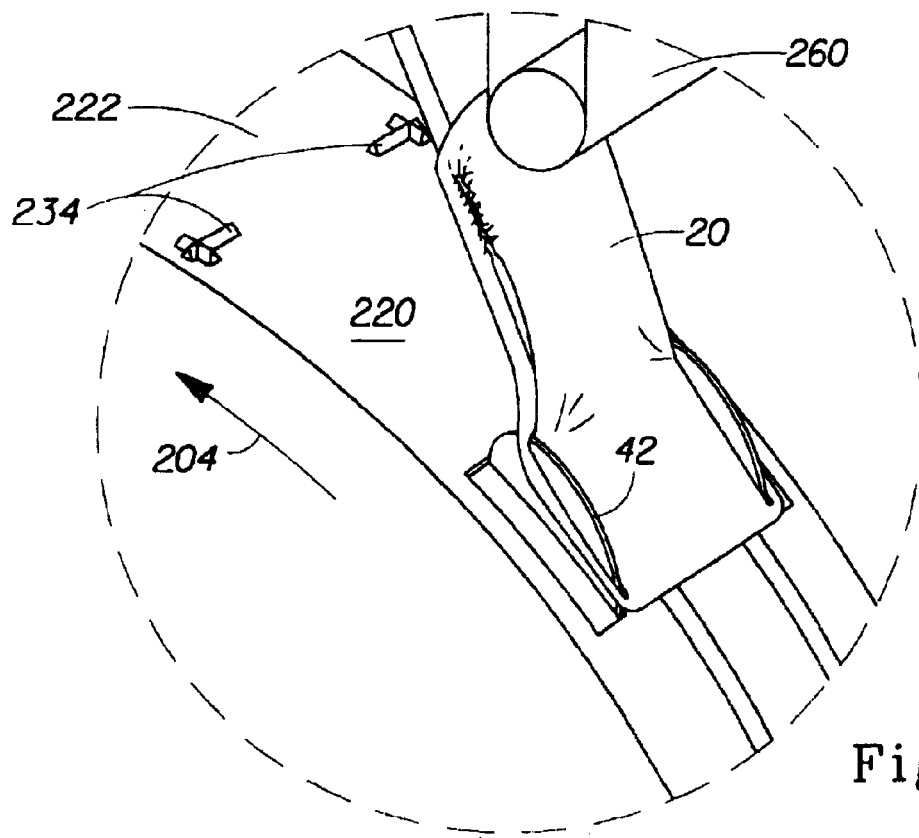
FIG. 18 is an enlarged view of circled area 18 of FIG. 7a, showing the diaper in its instant position of pulling off the diaper by a take-away conveyor to complete the insertion of the tab member through the slot of the slot member to effect the engagement.

Further, while the portion 47 of the tab member 42 is clamped to the drum 222, the article 20 can be partially lifted from the peripheral surface 220 of the drum 222 (as shown in FIG. 18) by a conveyor 260, or any other suitable device, after deactivating the center-fold clamps 234 releasing the article 20 along the fastening centerline 120, and also after deactivating the drum holding force 224 releasing the trailing part 124 of the article 20 from the peripheral surface 220 of the drum 222. While the portion 47 of the tab member 42 continues to be attached to the drum 222 by the clamp 246, the article 20 can be lifted from the peripheral surface 220 of the drum 222. By lifting the article 20, the slot 46 of the slot member 44 of the article 20 can move in relation to the tab member 42 until the slot 46 passes beyond the lip portion 48 of the tab member 42. In this configuration, the lip portion 48 of the tab member 42 will prevent the tab member 42 from slipping back through the slot 46 and disengaging the fastening system 40. After completing the engagement, the tab member 42 can be released from the drum 222 by deactivating the clamp 246, and the conveyor 260 can complete lifting the article 20 from the drum 222. The lifted article 20 can now have a closed configuration 262 (see FIG. 2) of the slot-and-tab fastener system 40 forming a pre-fastened article 20. The conveyor 260 can then transport the pre-fastened article 20 to downstream process operations.

Figure 19:
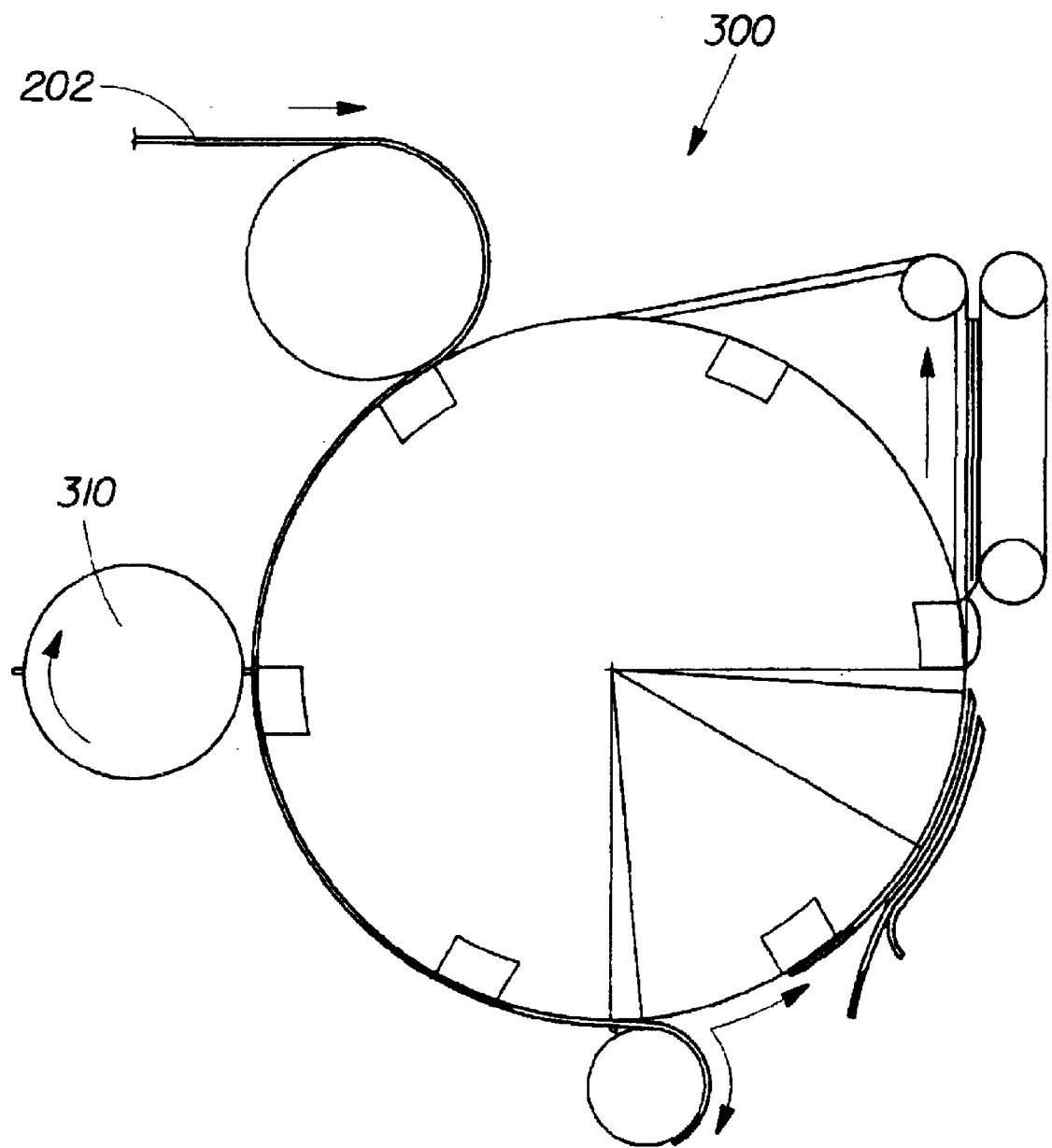
FIG. 19 is a simplified front elevation view of another embodiment of an apparatus of the present invention.

Alternatively to the embodiment 200 shown in FIG. 7, wherein the web 202 can be cut into individual articles 20 by the rotary cutter 212 prior to depositing the individual articles onto the peripheral surface 220 of the drum 222, FIG. 19 shows another embodiment 300 of the present invention. In the embodiment 300, the web 202 can be deposited onto and secured to the peripheral surface 220 of the drum 222 and then cut into individual articles 20 by any suitable cutting device, for example, a rotary cutter 310 cutting against the peripheral surface 220 of the drum 222. The rest of the operations of the embodiment 300 can be the same as described herein above for the embodiment 200.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A method of dynamically pre-fastening disposable absorbent articles having a slot-and-tab fastening system as the articles are driven forward at a relatively high velocity along a predetermined path, the method comprising the steps of:
    (a) providing a disposable absorbent article being folded longitudinally into a bi-fold configuration;
    (b) inserting at least a portion of a tab member of the slot-and-tab fastening system through a slot of the slot-and-tab fastening system by positioning the slot member with a slot locator and by guiding the tab member with a guiding rail and a folding board;
    (c) while holding the portion of the tab member being inserted through the slot, moving the slot member of the article opposite to the direction of insertion of the portion of the tab member until the slot of the slot member passes beyond a lip portion of the tab member to effect a complete insertion of the tab member through the slot member and to effect a closed configuration of the slot-and-tab fastening system forming a pre-fastened disposable absorbent article,
    wherein the pre-fastened disposable absorbant article is traveling in a machine direction at a rate of at least 200 feet per minute.

2. The method according to claim 1 wherein the pre-fastened disposable absorbent article is traveling at a rate from about 200 feet per minute to about 1,000 feet per minute.

* * * * *